United States Patent [19]

Jost

[11] Patent Number: Plant 6,045

[45] Date of Patent: Oct. 27, 1987

[54] PEACH TREE (SIERRA LADY)

[76] Inventor: Michael D. Jost, 1262 S. Rupert St., Reedley, Calif. 93654

[21] Appl. No.: 806,267

[22] Filed: Dec. 6, 1985

[51] Int. Cl.[4] ..... A01H 5/03
[52] U.S. Cl. ..... Plt./43
[58] Field of Search ..... Plt./43

*Primary Examiner*—Robert E. Bagwill

*Attorney, Agent, or Firm*—William H. Meserole; Roger B. Webster

[57] ABSTRACT

The present variety of peach tree is a comparatively early ripening mutation of the O'Henry, and is characterized by a tree of medium to large size, medium vigor, and the regular and very productive bearing of highly colored, well-sized, fully freestone, fine textured fruit of very good flavor and superior eating quality; the fruit ripening substantially two weeks earlier than the O'-Henry.

1 Drawing Figure

BACKGROUND OF THE VARIETY

Field of the Invention

In connection with my activities in the operation of a family ranch, including an orchard, located near Reedley, Fresno County, Calif., I frequent such ranch and orchard during routine agricultural operations, including cultivation, irrigation, and harvesting of crops. Against this background of my activities, the present variety of peach tree was discovered by me.

CLASSIFICATION OF THE VARIETY

The present variety of peach tree is embraced by Class 43, Plants, of the U.S. Patent Office Manual of Classification.

PRIOR VARIETIES

Among existing varieties of peach trees which are known to me is the O'Henry (U.S. Plant Pat. No. 2,964), and which variety is mentioned herein for the purpose of comparison.

ORIGIN OF THE VARIETY

The present variety of peach tree was discovered by me growing as a small limb (hanger) on a scaffold of a peach tree of the O'Henry variety growing in the orchard located as aforesaid; it having been observed by me that such small limb bore fruit which was full ripe well ahead of the date of ripening of the fruit of the remainder of such tree. After its discovery, I maintained the mutation under close and continuing observation in order to confirm such earlier ripening of the fruit. Upon such confirmation, I determined to asexually reproduce the discovered mutation in contemplation of its potential commercialization.

ASEXUAL REPRODUCTION OF THE VARIETY

The present variety of peach tree was asexually reproduced, under my direction and on my behalf, by a commercial nursery, by budding on seedling "Nemaguard" peach rootstock; the reproductions then having been planted and grown in an orchard on the aforesaid ranch. In maturity the reproductions ran true to the original mutation in all respects.

SUMMARY OF THE VARIETY

The present variety of peach tree — with the exception of fruit maturity differences — is phenotypically very similar to the O'Henry, and is characterized by a tree of medium to large size, medium vigor, and the regular and very productive bearing of highly colored, well-sized, fully freestone, fine textured, fruit of very good flavor and superior eating quality.

The present variety of peach tree is further — and distinctively — characterized, in comparison to the O'Henry, by fruit which ripens and is in harvest substantially two weeks earlier than the O'Henry.

BRIEF DESCRIPTION OF THE DRAWING

The drawing is an illustration, by photographic reproduction in color, of a twig with leaves, a separate leaf, and separate fruit; one of the latter being cut into halves with the stone remaining in one half.

DESCRIPTION OF THE VARIETY

The botanical details of the present variety of peach tree — with color definitions (except those in common color terms) referenced to the 1950 edition of Maerz and Paul Dictionary of Color — are as follows:

Tree:
- *Size.*—Medium to large.
- *Vigor.*—Vigorous.
- *Growth.*—Upright Spreading.
- *Hardiness.*—Hardy under typical growing conditions in Central Valley of California.
- *Production.*—Very productive.
- *Bearing.*—Regular bearer.

Trunk:
- *Size.*—Medium thickness.
- *Texture.*—Medium.
- *Color.*—Mature Bark — brownish-grey (15-A-9).
- *Lenticels.*—Number — average.

Branches:
- *Size.*—Medium.
- *Texture.*—Medium to smooth.
- *Color.*—Young branches, light green (19-I-4). Mature branches, brown (7-E-10).
- *Lenticels.*—Number — average.

Leaves:

*Size.*—(at midpoint of vigorous upright current seasons shoots). Large. Average length — 20.0 cm. Average width — 4.2 cm. Average thickness for species.

*Texture.*—Smooth.

*Form.*—Lanceolate. Tip acuminate — slightly twisted.

*Color.*—Top side — dark green (24-J-8). Under side — grey-green (23-H-5).

*Margin.*—Coarsely crenate, at times doubly so moderately undulate.

*Petiole.*—Medium to slightly long. Average length — 9.0 mm. Average thickness — 1.5 to 2.0 mm. Light grey-green (21-J-1).

*Glands.*—Medium size. Reniform. Range number — 3-6, located alternately on base of leaf margin and petiole. Commonly 2 to 3 glands on base of leaf blade and 2 to 3 glands on petiole. Yellow-green (20-J-2) and shiny, darkening with maturity.

*Stipules.*—Medium to small. Average — 4 to 4.5 mm. in length. Located at base of petiole. Light yellow-green (20-I-4), darkening and often becoming tinged with red with advancing maturity. Early deciduous.

Flower buds: Hardy under typical growing conditions in Central Valley of California. Medium size. Conic. Moderately plump. Free from stem. Pubescent.

Flowers: Similar to O'Henry. Large. Pink. Slightly late in comparison to other commercial peach varieties, attaining full bloom in early March.

Fruit:

*Maturity when described.*—Full commercial maturity, approaching tree ripe.

*Date of first picking.*—July 20, 1985.

*Date of last picking.*—July 30, 1985.

*Size.*—Above medium to large. Average suture diameter — 69 mm. Average cheek diameter — 71 mm. Average axial diameter — 65 mm.

*Form.*—Uniform. Slightly asymmetrical, one-half commonly larger than other. Globose in apical aspect. Globose to moderately oblate in lateral aspect.

*Suture.*—Inconspicuous shallow line extending from base to apex and beyond apex 5 to 7 mm. Somewhat deeper over basal shoulder 15 to 17 mm. from basal scar, also slightly deeper near axial end. Marked depression beyond pistil point.

*Ventral surface.*—Round. Very slightly lipped. One side of fruit commonly slightly larger in size.

*Stem cavity.*—Broad. Open. Moderately shallow. Average depth — 10 to 12 mm. Average width — 20 mm. Average length — 25 mm. Round to slightly oval in basal aspect. Suture often visible only on ventral side of cavity.

*Base.*—Round to slightly truncate. At right angle to fruit axis.

*Apex.*—Rounded to slightly depressed. Pistil point depressed and apical.

*Stem.*—Medium size. Average length — 8 to 10 mm. Average thickness — 2.0 to 2.5 mm. Green (20-J-4).

Skin:

*Thickness.*—Average.

*Texture.*—Average.

*Tendency to crack.*—None observed.

*Pubescence.*—Light. Short fibers.

*Color.*—Ground color — Yellow (11-I-6). Blush color — Red (6-L-10) to red-orange (4-K-11). Sun exposed areas darker purple-red (8-L-8).

Blush color extends over 95 to 100 percent of fruit surface, with ground color exposed over less than 5 percent of fruit surface.

Flesh:

*Color.*—Yellow (11-K-5) with moderate amount of red flecking in flesh. Pit cavity — Dark red (5-K-10).

*Amygdalin.*—Slight.

*Juice.*—Abundant.

*Flavor.*—Very good. Moderately acid. Well balanced.

*Aroma.*—Good. Very pleasant.

*Texture.*—Fine. Melting.

*Fibers.*—Average number. Tender.

*Ripens.*—Evenly.

*Eating quality.*—Superior. Rich and well-balanced flavor is among best of season.

Stone:

*Type.*—Full freestone. Retains some short fibers along basal shoulder of both ventral and dorsal sutures.

*Size.*—Small. Average length — 29.0 mm. Average width — 23.5 mm. Average thickness — 16.0 mm.

*Fibers.*—Few. Average length.

*Form.*—Oval to slightly obovate.

*Base.*—Oblique to central axis of stone, shorter on ventral suture edge.

*Hilum.*—Medium width. Oval.

*Apex.*—Rounded, with sharp tip.

*Sides.*—Usually slightly unequal.

*Surface.*—Numerous grooves and pits with relatively flattened ridges. Finely grooved and furrowed over basal shoulders. Strong ridging near apical shoulder, especially near apical end of dorsal suture.

*Ridges.*—Moderately rounded especially in lateral mid-stone area.

*Pits.*—Variable, both circular and elongated types present.

*Ventral edge.*—Moderately thick with low wings converging apically.

*Dorsal edge.*—Moderately thick with prominent ridges and deep, wide groove from base to apical shoulder. Groove narrower and more shallow over apical shoulder. Ridges most prominent near mid-suture. Some erosion of dorsal suture just below apex.

*Color (dry stone).*—Dark brown (8-C-10) with purple staining especially over base and ventral suture.

*Tendency to split.*—None observed.

Use: Fresh market for both local and long distance shipping.

Keeping quality: Good.

Resistance to insects and diseases: No particular susceptibilities noted.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, which is phenotypically very similar to the O'Henry, but distinctively characterized, in comparative fruit maturity, by ripening substantially two weeks earlier.

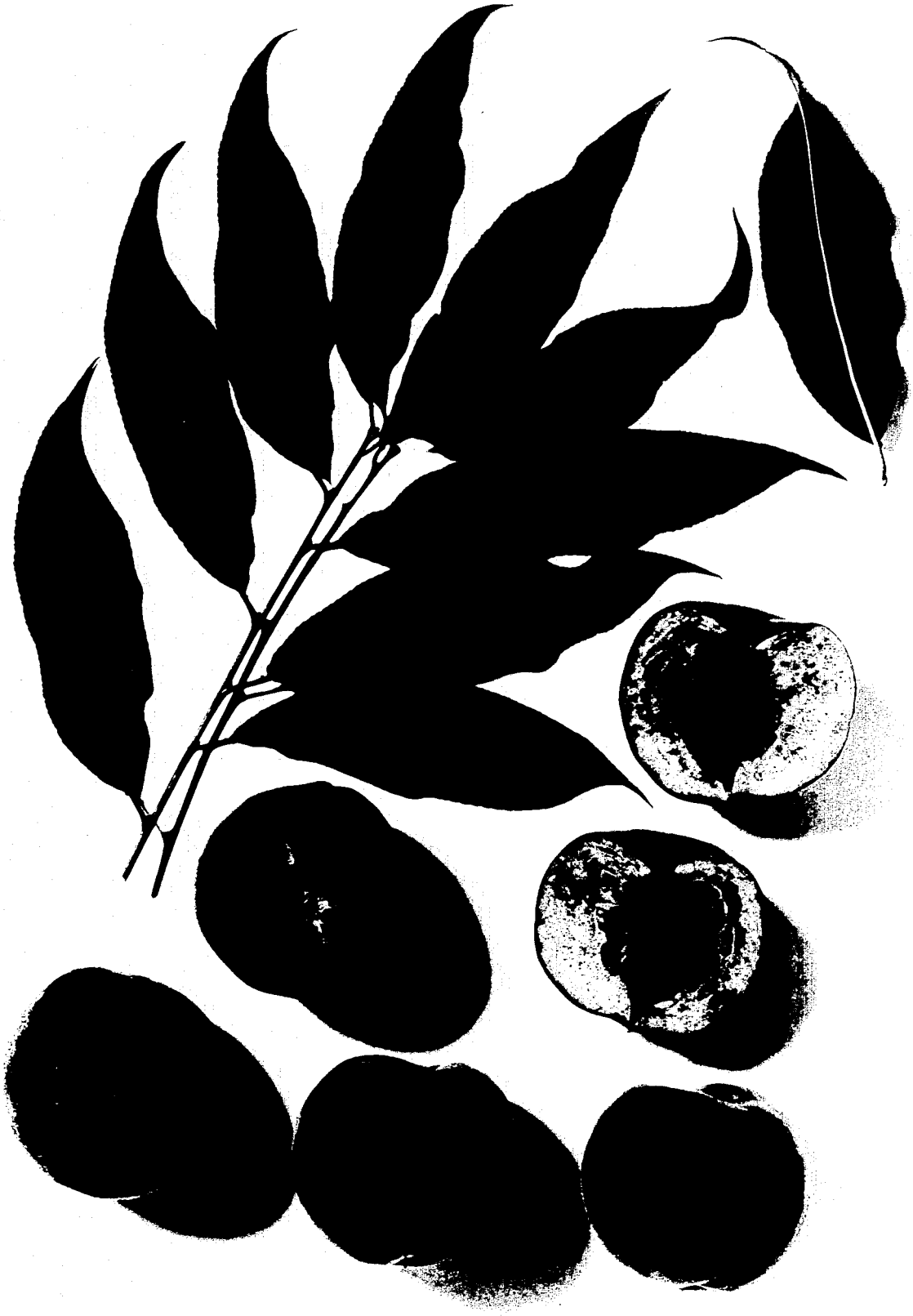

* * * * *